United States Patent
Schlueter

(10) Patent No.: US 7,799,845 B2
(45) Date of Patent: Sep. 21, 2010

(54) OPHTHALMIC AND OTORHINOLARYNGOLOGICAL DEVICE MATERIALS

(75) Inventor: Douglas C. Schlueter, Azle, TX (US)

(73) Assignee: Alcon, Inc., Hunenberg (CH)

( * ) Notice: Subject to any disclaimer, the term of this patent is extended or adjusted under 35 U.S.C. 154(b) by 242 days.

(21) Appl. No.: 12/244,843

(22) Filed: Oct. 3, 2008

(65) Prior Publication Data
US 2009/0093603 A1    Apr. 9, 2009

Related U.S. Application Data

(60) Provisional application No. 60/977,327, filed on Oct. 3, 2007.

(51) Int. Cl.
*G02B 1/04* (2006.01)
*A61F 2/16* (2006.01)

(52) U.S. Cl. ............... 523/106; 526/318.1; 526/319; 526/320; 526/321; 526/326; 526/328.5; 623/6.11; 623/6.56; 623/6.6

(58) Field of Classification Search ........... 523/106; 526/318.1, 319, 320, 321, 326, 328.5; 623/6.11, 623/6.56, 6.6
See application file for complete search history.

(56) References Cited

U.S. PATENT DOCUMENTS

| | | | |
|---|---|---|---|
| 5,290,892 A | 3/1994 | Namdaran et al. | |
| 5,331,073 A | 7/1994 | Weinschenk, III et al. | |
| 5,470,932 A | 11/1995 | Jinkerson | |
| 5,693,095 A | 12/1997 | Freeman et al. | |
| 5,763,548 A | 6/1998 | Matyjaszewski et al. | |
| 5,789,487 A | 8/1998 | Matyjaszewski et al. | |
| 5,852,129 A | 12/1998 | Kusakabe et al. | |
| 6,353,069 B1 | 3/2002 | Freeman et al. | |
| 6,528,602 B1 | 3/2003 | Freeman et al. | |
| 6,653,422 B2 | 11/2003 | Freeman et al. | |
| 7,390,863 B2 | 6/2008 | Salamone et al. | |
| 2005/0106117 A1 | 5/2005 | Adams et al. | |
| 2006/0134169 A1 | 6/2006 | Linhardt et al. | |
| 2006/0275342 A1 | 12/2006 | Linhardt et al. | |

FOREIGN PATENT DOCUMENTS

| | | |
|---|---|---|
| WO | WO9724382 | 10/1997 |
| WO | WO2006130402 A2 | 7/2006 |
| WO | WO2006138188 A1 | 12/2006 |
| WO | WO2006138213 A1 | 12/2006 |

OTHER PUBLICATIONS

Norman, et al., Synthesis of Well-Defined Macromonomers by Sequential ATRP-Catalytic Chain Transfer and Copolymerization with Ethyl Acrylate, Macromolecules 2002, 8954-8961, 35 (24), ACS Publications, Washington, DC.
Bon, et al., Modification of the w-Bromo End Group of Poly (methacrylate)s Prepared by Copper (I)-Mediated Living Radical Polymerization. Journal of Polymer Science: Part A: Polymer Chemistry, 2000, 2678-2686, 38, John Wiley & Sons, Inc.
Phan, et al., Amphiphilic Block Copolymers PS-b-PEO-b-PS: Synthesis by ATRP and Thermal Behaviour Characterization, Polymer Preprints 2005, 138-139, 46(2).
Siegwart, et al., Solvent Induced Morphologies of PMMA-PEO-PMMA Triblock Copolymers Synthesized by ATRP, Polymer Preprints 2005, 399-400, 46(2).
Jankova, et al., Synthesis of Amphiphilic PS-b-PEG-b-PS by Atom Transfer Radical Polymerization, Macromolecules 1998, 538-541, 31(2).
Truelson, et al., Novel Polymeric Surfactants Synthesized by Atom Transfer Radical Polymerization, Polymer Preprints 2002, 49-50, 43(2).
Even, et al., Synthesis and Characterization of Amphiphilic Triblock Polymers by Copper Mediated Living Radical Polymerization, European Polymer Journal 2003, 633-639, 39.

*Primary Examiner*—David Wu
*Assistant Examiner*—Vu A Nguyen
(74) *Attorney, Agent, or Firm*—Patrick M. Ryan

(57) ABSTRACT

Disclosed are soft, high refractive index, acrylic device materials. The materials comprise di-block or tri-block macromers containing a hydrophilic block in the polymer backbone. The materials have improved glistening resistance.

20 Claims, No Drawings

OPHTHALMIC AND OTORHINOLARYNGOLOGICAL DEVICE MATERIALS

This application claims priority to U.S. Provisional Application Ser. No. 60/977,327 filed Oct. 3, 2007.

FIELD OF THE INVENTION

This invention is directed to improved ophthalmic and otorhinolaryngological device materials. In particular, this invention relates to soft, high refractive index acrylic device materials that have improved glistening resistance.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Conventional silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than conventional silicone materials.

U.S. Pat. No. 5,290,892 discloses high refractive index, acrylic materials suitable for use as an intraocular lens ("IOL") material. These acrylic materials contain, as principal components, two aryl acrylic monomers. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable, high refractive index ophthalmic lens materials containing at least about 90 wt. % of only two principal components: one aryl acrylic hydrophobic monomer and one hydrophilic monomer. The aryl acrylic hydrophobic monomer has the formula

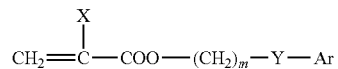

wherein:
X is H or CH$_3$;
m is 0-6;
Y is nothing, O, S, or NR, wherein R is H, CH$_3$, C$_n$H$_{n+1}$ (n=1–10), iso-OC$_3$H$_7$, C$_6$H$_5$, or CH$_2$C$_6$H$_5$; and
Ar is any aromatic ring which can be unsubstituted or substituted with CH$_3$, C$_2$H$_5$, n-C$_3$H$_7$, iso-C$_3$H$_7$, OCH$_3$, C$_6$H$_{11}$, Cl, Br, C$_6$H$_5$, or CH$_2$C$_6$H$_5$.

The lens materials described in the '095 patent preferably have a glass-transition temperature ("T$_g$") between about −20 and +25° C.

Flexible intraocular lenses may be folded and inserted through a small incision. In general, a softer material may be deformed to a greater extent so that it can be inserted through an increasingly smaller incision. Soft acrylic or methacrylic materials typically do not have an appropriate combination of strength, flexibility and non-tacky surface properties to permit IOLs to be inserted through an incision as small as that required for silicone IOLs.

Polyethylene glycol (PEG) dimethacrylates are known to improve glistening resistance of hydrophobic acrylic formulations. See, for example, U.S. Pat. Nos. 5,693,095; 6,528,602; 6,653,422; and 6,353,069. Both the concentration and molecular weight of PEG dimethacrylates have an impact on glistening performance. Generally, use of higher molecular weight PEG dimethacrylates (1000 MW) yield copolymers with improved glistening performance at low PEG concentrations (10-15 wt %), as compared to lower molecular weight PEG dimethacrylates (<1000 MW). However, low PEG dimethacrylate concentrations are desirable to maintain a high refractive index copolymer. Addition of PEG dimethacrylates also tends to decrease the modulus and tensile strength of the resulting copolymer. Also, higher molecular weight PEG dimethacrylates are generally not miscible with hydrophobic acrylic monomers.

SUMMARY OF THE INVENTION

Improved soft, foldable acrylic device materials which are particularly suited for use as IOLs, but which are also useful as other ophthalmic or otorhinolaryngological devices, such as contact lenses, keratoprostheses, corneal rings or inlays, otological ventilation tubes and nasal implants, have been discovered. These polymeric materials comprise di-block or tri-block macromers containing a hydrophilic block in the polymer backbone.

The specified block architecture of the macromer of the present invention permits solubilization of higher molecular weight hydrophilic blocks in a hydrophobic monomer formulation prior to polymerization. Higher molecular weight hydrophilic blocks provide glistening resistance at lower hydrophilic block concentrations compared to lower molecular weight hydrophilic blocks. The presence of the hydrophobic block composition in the macromer increases the macromer's solubility in a hydrophobic copolymer formulation. This resulting hydrophilic ingredient concentration reduction results in reduced equilibrium water content, higher refractive index, and a smaller mass intraocular lens that can be inserted through a smaller incision. The subject di-block and tri-block macromers allow synthesis of glistening resistant, low equilibrium water content, high refractive index IOLs.

DETAILED DESCRIPTION OF THE INVENTION

Unless indicated otherwise, all component amounts are presented on a % (w/w) basis ("wt. %").

The device materials of the present invention are copolymers comprising a) a monofunctional acrylate or methacrylate monomer [1], b) a difunctional acrylate or methacrylate cross-linker [2], and c) a di-block or tri-block macromer [3] (which may be a macromer of formula [3a], [3b], [3c], [3d], or [3e]). The device materials may contain more than one monomer [1], more than one monomer [2], and more than one macromer [3]. Unless indicated otherwise, references to each ingredient are intended to encompass multiple monomers or macromers of the same formula and references to amounts are intended to refer to the total amount of all monomers or macromers of each formula.

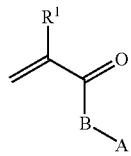
[1]

wherein
B=—O(CH$_2$)$_n$—, —(OCH$_2$CH$_2$)$_n$—, —NH(CH$_2$)$_n$—, or —NCH$_3$(CH$_2$)$_n$—;
R$^1$=H, CH$_3$, CH$_2$CH$_3$, or CH$_2$OH;
n=0-12;
A=C$_6$H$_5$ or O(CH$_2$)$_m$C$_6$H$_5$, where the C$_6$H$_5$ group is optionally substituted with —(CH$_2$)$_n$H, —O(CH$_2$)$_n$H, —CH(CH$_3$)$_2$, —C$_6$H$_5$, —OC$_6$H$_5$, —CH$_2$C$_6$H$_5$, F, Cl, Br, or I; and
m=0-18;

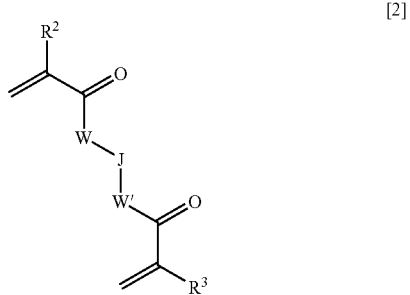
[2]

wherein
R$^2$, R$^3$ independently=H, CH$_3$, CH$_2$CH$_3$, or CH$_2$OH;
W, W' independently=O(CH$_2$)$_d$, NH(CH$_2$)$_d$, NCH$_3$(CH$_2$)$_d$, O(CH$_2$)$_d$C$_6$H$_4$, O(CH$_2$CH$_2$O)$_d$CH$_2$, O(CH$_2$CH$_2$CH$_2$O)$_d$CH$_2$, O(CH$_2$CH$_2$CH$_2$CH$_2$O)$_d$CH$_2$, or nothing;
J=(CH$_2$)$_a$, O(CH$_2$CH$_2$O)$_b$, O, or nothing, provided that if W and W'=nothing, then J≠nothing;
d=0-12;
a=1-12;
b=1-24;

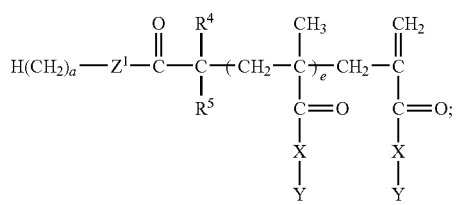
[3a]

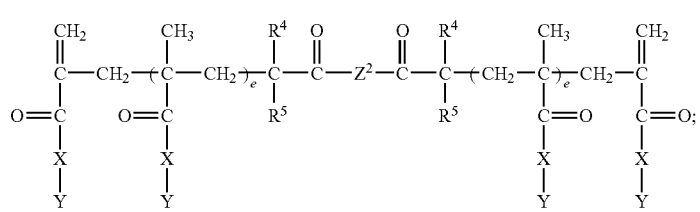
[3b]

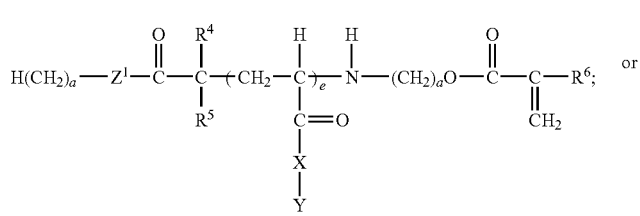
[3c]

or

-continued

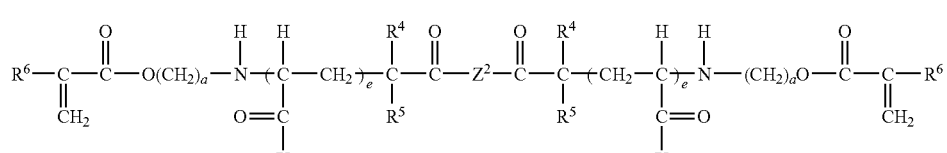

[3d]

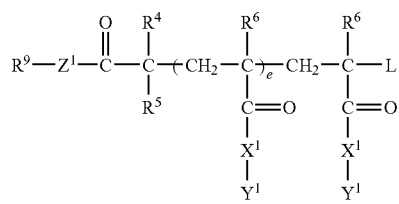

[3e]

wherein for formulas [3a], [3b], [3c], [3d], and [3e] (collectively, "formula [3]")
a independently=1-18;
$Z^1$=—(OCH$_2$CH$_2$)$_p$O—, —(OCH$_2$CH(CH$_3$))$_p$O—, —(NHCH$_2$CH$_2$)$_p$NH—, or —N(COR$^7$)CH$_2$CH$_2$)$_p$O;
X=O, NH—, N(CH$_3$)—, N(CH$_2$CH$_3$)—, or N(C$_6$H$_5$)—;
Y=—(CH$_2$)$_a$H, —CH$_2$C(CH$_3$)$_2$; —CH$_2$CH$_2$N(C$_6$H$_5$)$_2$, —CH$_2$CH(OH)CH$_2$OC$_6$H$_5$, —(CH$_2$CH$_2$O)$_p$C$_6$H$_5$, —(CH$_2$)$_t$C$_6$H$_5$, or —(CH$_2$)$_t$OC$_6$H$_5$;
$Z^2$=(OCH$_2$CH$_2$)$_p$O—, —(OCH$_2$CH(CH$_3$))$_p$O—, —(NHCH$_2$CH$_2$)$_p$NH—, or —O(CH$_2$CH$_2$(COR$^7$)N)$_p$—R$^8$—(N(COR$^7$)CH$_2$CH$_2$)$_p$O—;
$R^4$, $R^5$, $R^6$ independently=H, CH$_3$, CH$_2$CH$_3$, CH$_2$CH$_2$CH$_3$, CH(CH$_3$)$_2$, CH$_2$CH$_2$CH$_2$CH$_3$, or CH$_2$CH(CH$_3$)$_2$;
$R^7$=CH$_3$, CH$_2$CH$_3$, CH$_2$CH$_2$CH$_3$, CH(CH$_3$)$_2$, CH$_2$CH$_2$CH$_2$CH$_3$, or CH$_2$CH(CH$_3$)$_2$;
$R^8$=CH$_2$, (CH$_2$)$_2$, (CH$_2$)$_3$, (CH$_2$)$_4$, (CH$_2$)$_5$, or (CH$_2$)$_6$;
p=1-500;
e=1-200, provided that p≧e;
t=0-6;
$R^9$=CH$_2$=C(R$^6$)C(O)—, CH$_2$=C(R$^6$)CO$_2$CH$_2$CH$_2$NHC(O)—, or CH$_2$=CHC$_6$H$_4$C(O)CH$_2$=CHC$_6$H$_4$CH$_2$; and
L=H, Cl, Br, —CH$_2$C(O)CH$_3$, CH$_2$C(O)C(CH$_3$)$_3$, —CH$_2$C(O)C$_6$H$_5$, —CH$_2$C(O)C$_6$H$_4$OH, —CH$_2$C(O)C$_6$H$_4$OCH$_3$,

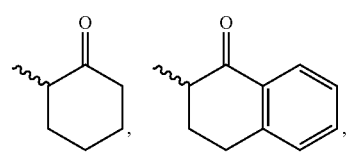

or CH$_2$CH=CH$_2$.

Preferred monomers of formula [1] are those wherein:
B=—O(CH$_2$)$_n$— or —(OCH$_2$CH$_2$)$_n$—;
$R^1$=—H or —CH$_3$;
n=1-5;
A=—C$_6$H$_5$, O(CH$_2$)$_m$C$_6$H$_5$; and
m=0-4.

Preferred monomers of formula [2] are those wherein:
$R^2$, $R^3$ independently=H or CH$_3$;
W, W' independently=O(CH$_2$)$_d$, O(CH$_2$)$_d$C$_6$H$_4$, or nothing;
J=O(CH$_2$CH$_2$O)$_b$ or nothing, provided that if W and W'=nothing, then J≠nothing;
d=0-6; and
b=1-10.

Preferred macromers of formula [3] are those wherein:
a independently=1-12;
$Z^1$=—(OCH$_2$CH$_2$)$_p$O—, or —(OCH$_2$CH(CH$_3$))$_p$O—;
X=O, or N(CH$_3$)—;
Y=—(CH$_2$)$_t$C$_6$H$_5$, or (CH$_2$)$_t$OC$_6$H$_5$;
$Z^2$=—(OCH$_2$CH$_2$)$_p$O—, or —(OCH$_2$CH(CH$_3$))$_p$O—;
$R^4$, $R^5$, $R^6$ independently=H, CH$_3$, or CH$_2$CH$_3$;
p=20-250;
e=5-150, provided that p≧e;
t=1-4;
$R^9$=CH$_2$=C(R$^6$)C(O)—, or CH$_2$=C(R$^6$)CO$_2$CH$_2$CH$_2$NHC(O)—; and
L=H, Cl, Br, —CH$_2$C(O)CH$_3$, CH$_2$C(O)C(CH$_3$)$_3$, —CH$_2$C(O)C$_6$H$_5$, —CH$_2$C(O)C$_6$H$_4$OH, —CH$_2$C(O)C$_6$H$_4$OCH$_3$,

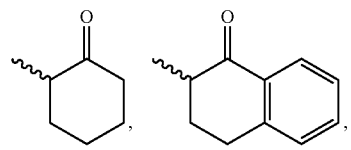

or CH$_2$CH=CH$_2$.

Most preferred macromers of formula [3] are those wherein:
a independently=1-4;
$Z^1$=—(OCH$_2$CH$_2$)$_p$O—;
X=O;
Y=(CH$_2$)$_t$C$_6$H$_5$;
$Z^2$=—(OCH$_2$CH$_2$)$_p$O—;
$R^4$, $R^5$=CH$_3$;
$R^6$=H or CH$_3$;
p=30-120;
e=10-100, provided that p is ≧e;
t=1-2;

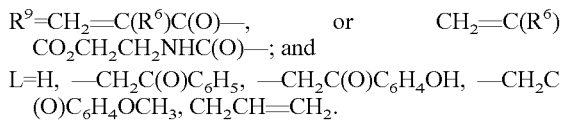

L=H, —CH$_2$C(O)C$_6$H$_5$, —CH$_2$C(O)C$_6$H$_4$OH, —CH$_2$C(O)C$_6$H$_4$OCH$_3$, CH$_2$CH=CH$_2$.

Monomers of formula [1] are known and can be made by known methods. See, for example, U.S. Pat. Nos. 5,331,073 and 5,290,892. Many monomers of formula [1] are commercially available from a variety of sources. Preferred monomers of formula [1] include benzyl methacrylate; 2-phenylethyl methacrylate; 3-phenylpropyl methacrylate; 4-phenylbutyl methacrylate; 5-phenylpentyl methacrylate; 2-phenoxyethyl methacrylate; 2-(2-phenoxyethoxy)ethyl methacrylate; 2-benzyloxyethyl methacrylate; 2-(2-(benzyloxy)ethoxy)ethyl methacrylate; and 3-benzyloxypropyl methacrylate; and their corresponding acrylates.

Monomers of formula [2] are known and can be made by known methods. Many are commercially available. Preferred monomers of formula [2] include ethylene glycol dimethacrylate; diethylene glycol dimethacrylate; triethylene glycol dimethacrylate; 1,6-hexanediol dimethacrylate; 1,4-butanediol dimethacrylate; 1,4-benzenedimethanol dimethacrylate; and their corresponding acrylates. Most preferred is 1,4-butanediol diacrylate.

Macromers of formula [3] can be made by known methods. Macromers of formula [3] can be made using controlled radical polymerization methods. For example, macromers of structure [3a] and [3b] may be prepared by atom transfer radical polymerization (ATRP) of methacrylic monomers using polyethylene glycol-based initiators. A monofunctional or difunctional PEG with terminal bromoisobutyrate group(s) is combined with copper(I) halide and a solubilizing amine ligand to polymerize a selected methacrylate monomer. Once the desired molecular weight has been obtained a radical scavenger or catalytic chain transfer reagent is added to produce a methacrylic polymer with unsaturated end groups. See for example Norman, J. et al. *Macromolecules* 2002, 35, 8954-8961, or Bon, S. A. F. et al. *J. Polym. Sci., Polym. Chem.* 2000, 38, 2678.

Macromers of formula [3c] and [3d] may be prepared by atom transfer radical polymerization (ATRP) of methacrylic or acrylic monomers using polyethylene glycol-based initiators. In these cases, termination with a hydroxyl-functional primary amine yields a hydroxyl terminated poly(acrylate) or poly(methacrylate). This product can then be reacted with methacryloyl chloride or isocyanatoethyl methacrylate. See, generally, U.S. Pat. Nos. 5,852,129, 5,763,548, and 5,789,487.

Macromers of structure [3e] may also be prepared by atom transfer radical polymerization (ATRP). For example, a methacrylate monomer is combined with copper(I) halide, amine ligand and solvent. Polymerization is initiated with a mono-protected polyethylene glycol-based activated alkyl halide. Once the desired conversion has been achieved, an end-capping agent is added to produce a methacrylic polymer with desired terminal end group functionality. The protecting group is then removed from the polyethylene glycol-based initiator and the product polymer is esterified with, for example, methacryloyl chloride or isocyantoethyl methacrylate.

In a preferred embodiment, macromer [3] has the structure:

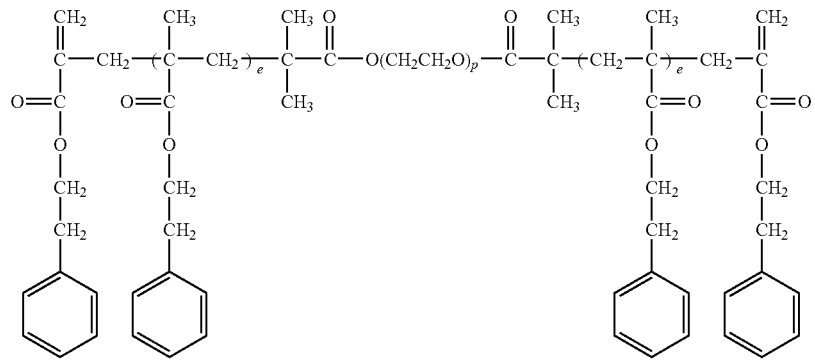

This macromer can be synthesized in two steps from poly (ethylene glycol) (M$_n$ 1500) as in Example 1 below. In the first step, poly(ethylene glycol) is esterified with 2-bromoisobutyryl bromide in the presence of pyridine. The purified product is then used to initiate polymerization of 2-phenylethyl methacrylate (PEMA) by ATRP, and the polymerization is terminated with a radical scavenger to create unsaturated end groups.

The copolymeric materials of the present invention contain a total amount of monomer [1] in an amount from 65 to 95%, and preferably from 70 to 90%. The difunctional cross-linker [2] concentration can be on the order of 0.5 to 3% of the total concentration, and preferably from 1 to 2%.

The materials of the present invention have at least one macromer of formula [3]. The total amount of macromer [3] depends on the desired physical properties for the device materials. The copolymeric materials of the present invention contain a total of at least 5 wt % and can contain as much as 35% of macromer [3]. Preferably, the copolymeric device materials will contain 10-30 wt % of macromer [3]. Most preferably, the copolymeric device materials will contain 10-20 wt % of macromer [3].

The copolymeric device materials of the present invention optionally contain one or more ingredients selected from the group consisting of polymerizable UV absorbers and polymerizable colorants. Preferably, the device material of the present invention contains no other ingredients besides the monomers of formulas [1] and [2], the macromer [3], and the optional polymerizable UV absorbers and polymerizable colorants.

Reactive UV absorbers are known. A suitable reactive UV absorber is 2-(2'-hydroxy-3'-methallyl-5'-methylphenyl)benzotriazole, commercially available as o-Methallyl Tinuvin P ("oMTP") from Polysciences, Inc., Warrington, Pa. UV absorbers are typically present in an amount from about 0.1-5%. Suitable reactive blue-light absorbing compounds include those described in U.S. Pat. No. 5,470,932. Blue-light absorbers are typically present in an amount from about 0.01-

0.5%. When used to make IOLs, the device materials of the present invention preferably contain both a reactive UV absorber and a reactive colorant.

In order to form the device material of the present invention, the chosen ingredients [1], [2], and [3], along with any of the optional ingredients, are combined and polymerized using a radical initiator to initiate polymerization by the action of either heat or radiation. The device material is preferably polymerized in de-gassed polypropylene molds under nitrogen or in glass molds.

Suitable polymerization initiators include thermal initiators and photoinitiators. Preferred thermal initiators include peroxy free-radical initiators, such as t-butyl (peroxy-2-ethyl) hexanoate and di-(tert-butylcyclohexyl) peroxydicarbonate (commercially available as Perkadox® 16 from Akzo Chemicals Inc., Chicago, Ill.). Particularly in cases where the materials of the present invention do not contain a blue-light absorbing chromophore, preferred photoinitiators include benzoylphosphine oxide initiators, such as 2,4,6-trimethylbenzoyldiphenyl-phosphine oxide, commercially available as Lucirin® TPO from BASF Corporation (Charlotte, N.C.). Initiators are typically present in an amount equal to about 5% or less of the total formulation weight, and more preferably less than 2% of the total formulation. As is customary for purposes of calculating component amounts, the initiator weight is not included in the formulation weight % calculation.

The particular combination of the ingredients described above and the identity and amount of any additional components are determined by the desired properties of the finished device material. In a preferred embodiment, the device materials of the present invention are used to make IOLs having an optic diameter of 5.5 or 6 mm that are designed to be compressed or stretched and inserted through surgical incision sizes of 2 mm or less. For example, the macromonomer [3] is combined with a mono-functional acrylate or methacrylate monomer [1], a multifunctional acrylate or methacrylate cross-linker [2], a reactive UV absorber and a reactive colorant and copolymerized using a radical initiator in a suitable lens mold.

The device material preferably has a refractive index in the hydrated state of at least about 1.50, and more preferably at least about 1.53, as measured by an Abbe' refractometer at 589 nm (Na light source) and 25° C. Optics made from materials having a refractive index lower than 1.50 are necessarily thicker than optics of the same power which are made from materials having a higher refractive index. As such, IOL optics made from materials with comparable mechanical properties and a refractive index lower than about 1.50 generally require relatively larger incisions for IOL implantation.

The proportions of the monomers and macromer to be included in the copolymers of the present invention should be chosen so that the copolymer has a glass transition temperature ($T_g$) not greater than about 37° C., which is normal human body temperature. Copolymers having glass transition temperatures higher than 37° C. are not suitable for use in foldable IOLs; such lenses could only be rolled or folded at temperatures above 37° C. and would not unroll or unfold at normal body temperature. It is preferred to use copolymers having a glass transition temperature somewhat below normal body temperature and no greater than normal room temperature, e.g., about 20-25° C., in order that IOLs made of such copolymers can be rolled or folded conveniently at room temperature. $T_g$ is measured by differential scanning calorimetry at 10° C./min., and is determined at the midpoint of the transition of the heat flux curve.

For IOLs and other applications, the materials of the present invention must exhibit sufficient strength to allow devices made of them to be folded or manipulated without fracturing. Thus the copolymers of the present invention will have an elongation of at least 80%, preferably at least 100%, and most preferably greater than 110%. This property indicates that lenses made of such materials generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions using an Instron Material Tester (Model No. 4442 or equivalent) with a 50 Newton load cell. The grip distance is set at 14 mm and a crosshead speed is set at 500 mm/minute and the sample is pulled until failure. The elongation (strain) is reported as a fraction of the displacement at failure to the original grip distance. Since the materials to be tested are essentially soft elastomers, loading them into the Instron machine tends to make them buckle. To remove the slack in the material sample a pre-load is placed upon the sample. This helps to reduce the slack and provide a more consistent reading. Once the sample is pre-loaded to a desired value (typically 0.03 to 0.05 N) the strain is set to zero and the test begun. The modulus is calculated as the instantaneous slope of the stress-strain curve at 0% strain ("Young's modulus"), 25% strain ("25% modulus") and 100% strain ("100% modulus).

IOLs made of the ophthalmic device materials of the present invention are more resistant to glistenings than other materials. Glistenings are measured according to the following test. The presence of glistenings is measured by placement of a lens or disk sample into a vial or sealed glass chamber and adding deionized water or a balanced salt solution. The vial or glass chamber is then placed into a water bath preheated to 45° C. Samples are to be maintained in the bath for a minimum of 16 hours and preferably 24±2 hours. The vial or glass chamber is then cooled to ambient temperature for a minimum of 60 minutes and preferably 90±30 minutes. The sample is inspected visually in various on angle or off angle lighting to evaluate clarity. Visualization of glistenings is carried out at ambient temperature with a light microscope using a magnification of 50 to 200×. A sample is judged to have many glistenings if, at 50-200× magnification, there are approximately 50 to 100% as many glistenings as observed in control samples based on 65 weight % 2-phenylethyl acrylate, 30 weight % 2-phenylethyl methacrylate, 3.2 weight % BDDA, and 1.8 weight % OMTP. Similarly, a sample is judged to have few glistenings if there are approximately 10% or more glistenings relative to the quantity observed in control samples. A sample is judged to have very few glistenings if there are approximately 1% or more glistenings relative to a control sample. A sample is judged to be free of glistenings if the number of glistenings detected in the eyepiece is zero. A sample is judged to be substantially free of glistenings if, at 50-200× magnification, the number of glistenings detected in the eyepiece is less than about $2/mm^3$. It is often very difficult to detect glistenings, especially at surfaces and edges where more defects and debris have formed, so the sample is rastered throughout the entire volume of the lens, varying the magnification levels (50-200×), the aperture iris diaphragm, and the field conditions (using both bright field and dark field conditions) in an attempt to detect the presence of glistenings.

The copolymers of the present invention most preferably have an equilibrium water content (EWC) of 0.5-3.0%. EWC may be gravimetrically determined by comparison of dry and hydrated sample weight. First, the dry sample weight is obtained, then the sample is placed in a suitable container and equilibrated in de-ionized $H_2O$ at a prescribed temperature for at least 24 h. The sample is then removed from the de-ionized $H_2O$, excess surface water is removed and the sample is weighed. EWC is determined by the following formula: % $EWC=[(wt_{hyd}-wt_{dry})/wt_{hyd}] \times 100$.

IOLs constructed of the device materials of the present invention can be of any design capable of being stretched or compressed into a small cross section that can fit through a 2-mm incision. For example, the IOLs can be of what is known as a one-piece or multi-piece design, and comprise optic and haptic components. The optic is that portion which serves as the lens and the haptics are attached to the optic and are like arms that hold the optic in its proper place in the eye. The optic and haptic(s) can be of the same or different material. A multi-piece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use as other ophthalmic or otorhinolaryngological devices such as contact lenses, keratoprostheses, corneal inlays or rings, otological ventilation tubes and nasal implants.

The invention will be further illustrated by the following examples, which are intended to be illustrative, but not limiting.

All monomers, cross-linkers, initiators and other chemicals were purchased from commercial sources. Polyethylene glycol (average $M_n$ 1500, 2000, 4600), and polyethylene glycol monomethylether (average $M_n$ 2000) were purchased from Aldrich and used as received. 2-Phenylethyl methacrylate (PEMA) and benzyl methacrylate (BZMA) were each passed through basic alumina and degassed with $N_2$ prior to use. 2-Phenylethyl acrylate (PEA), benzyl acrylate (BzA) and 1,4-butanediol diacrylate (BDDA) were purified by column chromatography prior to use. N,N,N',N',N''-pentamethyldiethylene triamine (PMDETA) was dried over calcium hydride and vacuum distilled prior to use. Acetone and toluene were each bubbled with $N_2$ and stored in the glove box. All reaction manipulations were performed in a $N_2$ filled glove box. 2,2-Azobisisobutyronitrile (AIBN) was recrystallized from methanol prior to use. All other chemicals were of highest purity available and used as received.

Example 1

Initiator Synthesis

Esterification of poly(ethylene glycol) (PEG) 1500 with 2-bromoisobutyrate

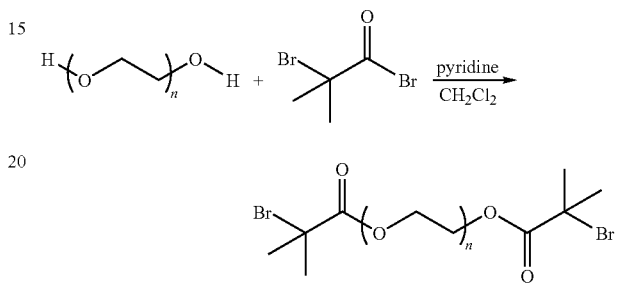

An oven dried 250 mL three-neck round bottom flask was fitted with 60 mL addition funnel with a $N_2$ inlet/outlet, and a thermometer adapter and glass stopper. The flask was charged with 29.0 g (19.3 mmol) of PEG 1500, 100 mL of anhydrous $CH_2Cl_2$ and 3.5 mL (43.2 mmol) of pyridine, and 5 mL (40.5 mmol) of 2-bromoisobutyryl bromide was placed in the addition funnel. The flask was closed and immersed in an ice bath. 2-Bromoisobutyryl bromide was added dropwise to the cooled solution over 20 min period with stirring. The ice bath was removed and the reaction was stirred for 64 h under a $N_2$ blanket. The reaction mixture was filtered and the filtrate was concentrated. The crude product was dissolved in a small amount of $CH_2Cl_2$, loaded onto a short basic alumina column and eluted with $CH_2Cl_2$. The eluent was collected and the solvent was removed using a rotary evaporator. The resulting solid was dissolved in $CH_2Cl_2$ and precipitated into a large excess of 1/1 hexane/diethyl ether. The product was dried overnight under vacuum to yield 20.6 g (59%) of a white powder.

Macromer Synthesis

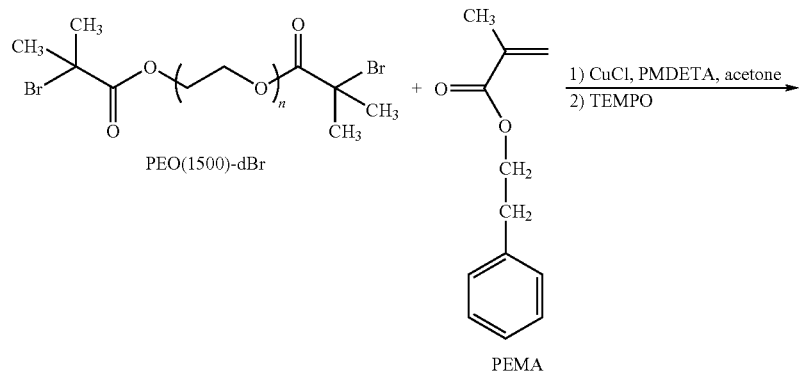

-continued

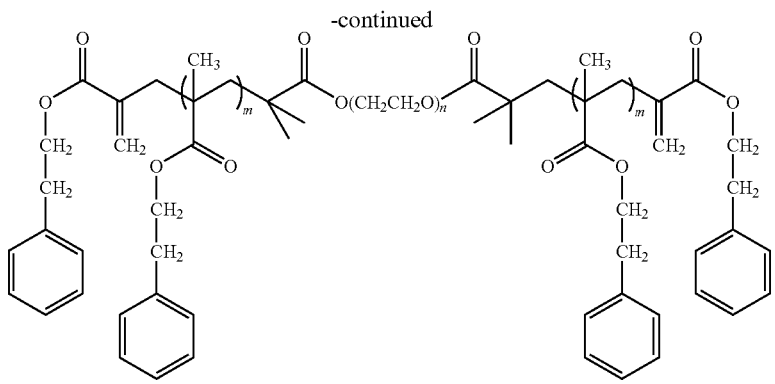

Poly(2-phenylethyl methacrylate)-block-poly(ethylene glycol)-block-poly(2-phenylethyl methacrylate) from PEG(1500) Difunctional Initiator. Target [M]/[I]=20

All synthetic manipulations were performed in a $N_2$-filled glove box. A 100 mL round bottom flask containing a PTFE-coated magnetic stirring bar was charged with 0.3622 g (3.66 mmol) of CuCl, 1.8026 g (10.17 mmol) of N,N,N',N',N''-pentamethyidiethylenetriamine, 12.8233 g (67.41 mmol) of 2-phenylethyl methacrylate (PEMA), and 20 mL of acetone. The flask was warmed to 50° C. in an oil bath. PEG(1500) difunctional initiator (5.0106 g, 3.34 mmol) was dissolved in acetone and was added to the stirring monomer solution. The reaction was maintained at 50° C. for 3 hrs. 2,2,6,6,-tetramethyl-1-piperidinyloxy (1.0621 g, 6.80 mmol) was dissolved in acetone and added to the reaction mixture. The reaction mixture was heated for an additional 1.5 hrs, then cooled overnight. The flask was removed from the glove box and bubbled with air for 30 min. The crude was concentrated by rotary evaporation, then diluted with $CH_2Cl_2$ and chromatographed over basic alumina using $CH_2Cl_2$ eluent. The eluent was collected and the solvent removed by rotary evaporation. The resulting polymer was dissolved in a small amount of $CH_2Cl_2$, and precipitated into a large excess of 1-propanol. The polymer was allowed to settle, the liquid fraction was decanted, and the polymer was rinsed with a fresh portion of 1-propanol. The product was again dissolved in $CH_2Cl_2$, transferred to a round bottom flask and the solvent was removed using a rotary evaporator. The product was dried further under vacuum overnight resulting in 6.05 g (34%) of a colorless viscous liquid.

Example 2

Initiator Synthesis

An oven dried 1 L three-neck round bottom flask was fitted with 60 mL addition funnel with a $N_2$ inlet/outlet, and a thermometer adapter and glass stopper. The flask was charged with 102.6 g (51.3 mmol) of PEG 2000, 300 mL of anhydrous $CH_2Cl_2$ and 8.5 mL (105.0 mmol) of pyridine, and 13 mL (105.0 mmol) of 2-bromoisobutyryl bromide was placed in the addition funnel. The flask was closed and immersed in an ice bath. 2-Bromoisobutyryl bromide was added dropwise to the cooled solution over 40 min period with stirring. The ice bath was removed and the reaction was stirred for 27 h under a $N_2$ blanket. The reaction mixture was filtered and the filtrate was concentrated. The crude product was dissolved in a small amount of $CH_2Cl_2$, loaded onto a short basic alumina column and eluted with $CH_2Cl_2$. The eluent was collected and the solvent was removed using a rotary evaporator. The resulting solid was dissolved in $CH_2Cl_2$ and precipitated into a large excess of 1/1 hexane/diethyl ether. The product was dried overnight under vacuum to yield 79.7 g (68%) of a white powder.

Macromer Synthesis

Poly(2-phenylethyl methacrylate)-block-poly(ethylene glycol)-block-poly(2-phenylethyl methacrylate) from PEG(2000) difunctional initiator. Target [M]/[I]=50

All synthetic manipulations were performed in a $N_2$-filled glove box. A 200 mL round bottom flask containing a PTFE-coated magnetic stirring bar was charged with 0.5542 g (5.60 mmol) of CuCl, 2.6753 g (15.09 mmol) of N,N,N',N',N''-pentamethyldiethylenetriamine, 46.4408 g (244.12 mmol) of 2-phenylethyl methacrylate (PEMA), and 50 mL of acetone. PEG(2000) difunctional initiator (9.9649 g, 4.98 mmol) was dissolved in 45 mL of acetone and was added to the stirring monomer solution. The reaction was stirred at ambient temperature for 19 hrs. 2,2,6,6,-tetramethyl-1-piperidinyloxy (1.5860 g, 10.15 mmol) was dissolved in acetone and added to the reaction mixture. The reaction mixture was immersed in a 50° C. oil bath and heated for 3 hrs, then cooled to ambient temperature. The flask was removed from the glove box and bubbled with air for 30 min. The crude was concentrated by rotary evaporation, then diluted with $CH_2Cl_2$ and chromatographed over basic alumina using $CH_2Cl_2$ mobile phase. The eluent was collected and the solvent removed by rotary evaporation. The resulting polymer was dissolved in a small amount of $CH_2Cl_2$, and precipitated into a large excess of 1-propanol. The polymer was allowed to settle, the liquid fraction was decanted, and the polymer was rinsed with a fresh portion of 1-propanol. The polymer was again dissolved in $CH_2Cl_2$, transferred to a round bottom flask and the solvent was removed using a rotary evaporator. The product was dried further under vacuum overnight resulting in 32.73 g (58%) of a colorless solid.

Example 3

Initiator Synthesis

An oven dried 500 mL three-neck round bottom flask was fitted with 60 mL addition funnel with a $N_2$ inlet/outlet, and a thermometer adapter and glass stopper. The flask was charged with 44.66 (9.8 mmol) of PEG 4600, 100 mL of anhydrous $CH_2Cl_2$ and 2.0 mL (24.7 mmol) of pyridine, and 2.6 mL (20.5 mmol) of 2-bromoisobutyryl bromide was placed in the addition funnel. The flask was closed and immersed in an ice bath. 2-Bromoisobutyryl bromide was added dropwise to the cooled solution over a 20 min period with stirring. The ice bath was removed and the reaction was stirred for 63 h under a $N_2$ blanket. The reaction mixture was filtered and the filtrate was concentrated. The crude product was dissolved in a small amount of $CH_2Cl_2$, loaded onto a short basic alumina column and eluted with $CH_2Cl_2$. The eluent was collected and the solvent was removed using a rotary evaporator. The resulting solid was dissolved in $CH_2Cl_2$ and precipitated into a large excess of 1/1 hexane/diethyl ether. The product was dried overnight under vacuum to yield 29.5 (62%) of a white powder.

Macromer Synthesis

Poly(2-phenylethyl methacrylate)-block-poly(ethylene glycol)-block-poly(2-phenylethyl methacrylate) from PEG(4600) difunctional initiator. Target [M]/[I]=67

All synthetic manipulations were performed in a $N_2$-filled glove box. A 200 mL round bottom flask containing a PTFE-coated magnetic stirring bar was charged with 0.2191 (2.21 mmol) of CuCl, 1.1108 (6.27 mmol) of N,N,N',N',N"-pentamethyldiethylenetriamine, 25.5245 (134.17 mmol) of 2-phenylethyl methacrylate (PEMA), and 40 mL of acetone. The flask was warmed to 50° C. in an oil bath. PEG(4600) difunctional initiator (9.8431 g, 2.01 mmol) was dissolved in acetone and was added to the stirring monomer solution. The reaction was maintained at 50° C. for 7 hrs. 2,2,6,6,-tetramethyl-1-piperidinyloxy (0.7234 g, 4.63 mmol) was dissolved in 40 mL of acetone and added to the reaction mixture. The reaction mixture was heated for an additional 30 min, then cooled overnight. The flask was removed from the glove box and bubbled with air for 30 min. The crude was concentrated by rotary evaporation, then diluted with $CH_2Cl_2$ and chromatographed over basic alumina using $CH_2Cl_2$ eluent. The eluent was collected and the solvent removed by rotary evaporation. The product was dissolved in a small amount of $CH_2Cl_2$, and precipitated into a large excess of 1-propanol. The polymer was allowed to settle, the liquid fraction was decanted, and the polymer was rinsed with a fresh portion of 1-propanol. The product was again dissolved in $CH_2Cl_2$, transferred to a round bottom flask and the solvent was removed using a rotary evaporator. The product was dried further under vacuum overnight resulting in 16.15 (47%) of a colorless soft solid.

Example 4

Initiator Synthesis

An oven dried 1 L three-neck round bottom flask was fitted with 60 mL addition funnel with a $N_2$ inlet/outlet, and a thermometer adapter and glass stopper. The flask was charged with 106.6 g (10.7 mmol) of PEG 4600, 300 mL of anhydrous $CH_2Cl_2$ and 2.0 mL (24.7 mmol) of pyridine, and 2.8 mL (22.1 mmol) of 2-bromoisobutyryl bromide was placed in the addition funnel. The flask was closed and immersed in an ice bath. 2-Bromoisobutyryl bromide was added dropwise to the cooled solution over a 20 min period with stirring. The ice bath was removed and the reaction was stirred for 63 h under a $N_2$ blanket. The reaction mixture was filtered and the filtrate was concentrated. The crude product was dissolved in a small amount of $CH_2Cl_2$, loaded onto a short basic alumina column and eluted with $CH_2Cl_2$. The eluent was collected and the solvent was removed using a rotary evaporator. The resulting solid was dissolved in $CH_2Cl_2$ and precipitated into a large excess of 1/1 hexane/diethyl ether. The product was dried overnight under vacuum to yield 83.8 (79%) of a white powder.

Macromer Synthesis

Poly(2-phenylethyl methacrylate)-block-poly(ethylene glycol)-block-poly(2-phenylethyl methacrylate) from PEG(10k) difunctional initiator. Target [M]/[I]=134

All synthetic manipulations were performed in a $N_2$-filled glove box. A 200 mL round bottom flask containing a PTFE-coated magnetic stirring bar was charged with 0.1296 g (1.31 mmol) of CuCl, 0.6828 (3.85 mmol) of N,N,N',N',N"-pentamethyldiethylenetriamine, 30.4780 g (160.21 mmol) of 2-phenylethyl methacrylate (PEMA), and 30 mL of acetone. PEG(10 k) difunctional initiator (12.0163 g, 1.17 mmol) was dissolved in 30 mL of acetone and was added to the stirring monomer solution. The reaction was stirred at ambient temperature for 21 hrs. 2,2,6,6,-tetramethyl-1-piperidinyloxy (0.4079 g, 2.61 mmol) was dissolved in acetone and added to the reaction mixture. The reaction mixture was immersed in a 50° C. oil bath and heated for 3 hrs, then cooled to ambient temperature. The flask was removed from the glove box and bubbled with air for 30 min. The crude was concentrated by rotary evaporation, then diluted with $CH_2Cl_2$ and chromatographed over basic alumina using $CH_2Cl_2$ mobile phase. The eluent was collected and the solvent removed by rotary evaporation. The resulting polymer was dissolved in a small amount of $CH_2Cl_2$, and precipitated into a large excess of 1-propanol. The polymer was allowed to settle, the liquid fraction was decanted, and the polymer was rinsed with a fresh portion of 1-propanol. The polymer was again dissolved in $CH_2Cl_2$, transferred to a round bottom flask and the solvent was removed using a rotary evaporator. The product was dried further under vacuum overnight resulting in 24.1 (57%) of a colorless solid.

Example 5

Initiator Synthesis

An oven dried 300 mL three-neck round bottom flask was fitted with 60 mL addition funnel with a $N_2$ inlet/outlet, and a thermometer adapter and glass stopper. The flask was charged with 36.42 g (18.2 mmol) of poly(ethylene glycol) methyl ether ($M_n$ 2000), 100 mL of anhydrous $CH_2Cl_2$ and 2.0 mL (24.7 mmol) of pyridine, and 2.4 mL (19.3 mmol) of 2-bromoisobutyryl bromide was placed in the addition funnel. The flask was closed and immersed in an ice bath. 2-Bromoisobutyryl bromide was added dropwise to the cooled solution over a 15 min period with stirring. The ice bath was removed and the reaction was stirred for 63 h under a $N_2$ blanket. The reaction mixture was filtered and the filtrate was concentrated. The crude product was dissolved in a small amount of $CH_2Cl_2$, loaded onto a short basic alumina column and eluted with $CH_2Cl_2$. The eluent was collected and the solvent was removed using a rotary evaporator. The resulting solid was dissolved in $CH_2Cl_2$ and precipitated into a large excess of 1/1 hexane/diethyl ether. The product was dried overnight under vacuum to yield 25.7 (66%) of a white powder.

Macromer Synthesis

Poly(2-phenylethyl methacrylate)-block-poly(ethylene glycol) from PEG(2000) Monofunctional Initiator. Target [M]/[I]=10

All synthetic manipulations were performed in a $N_2$-filled glove box. A 200 mL round bottom flask containing a PTFE-coated magnetic stirring bar was charged with 0.6562 g (6.63 mmol) of CuCl, 3.2117 g (18.11 mmol) of N,N,N',N',N"-pentamethyldiethylenetriamine, 11.7538 g (61.78 mmol) of 2-phenylethyl methacrylate (PEMA), and 30 mL of acetone. PEG(2000) monofunctional initiator (11.9978 g, 5.99 mmol) was dissolved in 15 mL of acetone and was added to the stirring monomer solution. The reaction was stirred at ambient temperature for 4.5 hrs. 2,2,6,6,-tetramethyl-1-piperidinyloxy (0.4079 g, 2.61 mmol) was dissolved in acetone and added to the reaction mixture. The reaction mixture was immersed in a 50° C. oil bath and heated for 30 min, then allowed to cool overnight. The flask was removed from the glove box and bubbled with air for 30 min. The crude was concentrated by rotary evaporation, then diluted with $CH_2Cl_2$ and chromatographed over basic alumina using $CH_2Cl_2$ mobile phase. The eluent was collected and the solvent removed by rotary evaporation. The resulting polymer was dissolved in a small amount of $CH_2Cl_2$, and precipitated into a large excess of 1-propanol. The polymer was allowed to settle, the liquid fraction was decanted, and the polymer was rinsed with a fresh portion of 1-propanol. The polymer was again dissolved in $CH_2Cl_2$, transferred to a round bottom flask and the solvent was removed using a rotary evaporator. The product was dried further under vacuum overnight resulting in 8.83 (37%) of a viscous liquid.

Example 6

Macromer Synthesis

Poly(benzyl methacrylate)-block-poly(ethylene glycol)-block-poly(benzyl methacrylate) from PEG (2000) monofunctional initiator. Target [M]/[I]=50

All synthetic manipulations were performed in a $N_2$-filled glove box. A 200 mL round bottom flask containing a PTFE-coated magnetic stirring bar was charged with 0.5470 g (5.53 mmol) of CuCl, 2.6808 g (15.12 mmol) of N,N,N',N',N"-pentamethyldiethylenetriamine, 46.1957 g (262.16 mmol) of benzyl methacrylate (BzMA), and 50 mL of acetone. PEG (2000) difunctional initiator from Ex. 2 (10.0700 g, 5.04 mmol) was dissolved in 30 mL of acetone and was added to the stirring monomer solution. The reaction was stirred at ambient temperature (22° C.) for 18 hrs. 2,2,6,6,-tetramethyl-1-piperidinyloxy (1.5926 g, 10.19 mmol) was dissolved in acetone and added to the reaction mixture. The reaction mixture was immersed in a 50° C. oil bath and heated for 3 hrs, then cooled to ambient temperature. The flask was removed from the glove box and bubbled with air for 35 min. The crude was concentrated by rotary evaporation, then diluted with $CH_2Cl_2$ and chromatographed over basic alumina using $CH_2Cl_2$ mobile phase. The eluent was collected and the solvent was removed by rotary evaporation. The resulting polymer was dissolved in a minimum amount of $CH_2Cl_2$, and precipitated into a large excess of 1-propanol. The polymer was allowed to settle, the liquid fraction was decanted, and the polymer was rinsed with a fresh portion of 1-propanol, then methanol. The polymer was again dissolved in $CH_2Cl_2$ and collected by precipitation into 5° C. methanol, filtered, and then rinsed with fresh methanol. The product was dried at ambient temperature under vacuum overnight resulting in 37.00 g (66%) of a white solid. GPC (THF, polystyrene standards) Mn 21,196, Mw/Mn 1.27.

Example 7

Macromer Synthesis

Poly(benzyl methacrylate)-block-poly(ethylene glycol)-block-poly(benzyl methacrylate) from PEG (2000) Monofunctional Initiator. Target [M]/[I]=134

All synthetic manipulations were performed in a $N_2$-filled glove box. A 200 mL round bottom flask containing a PTFE-coated magnetic stirring bar was charged with 0.2095 g (2.12 mmol) of CuCl, 1.1210 g (6.32 mmol) of N,N,N',N',N"-pentamethyldiethylenetriamine, 49.5893 g (281.42 mmol) of benzyl methacrylate (BzMA), and 50 mL of acetone. PEG (2000) difunctional initiator from Ex. 2 (4.0692 g, 2.03 mmol) was dissolved in 30 mL of acetone and was added to the stirring monomer solution. The reaction was stirred at ambient temperature (22° C.) for 22 hrs. 2,2,6,6,-tetramethyl-1-piperidinyloxy (0.6344 g, 4.06 mmol) was dissolved in acetone and added to the reaction mixture. The reaction mixture was immersed in a 50° C. oil bath and heated for 4 hrs, then cooled to ambient temperature. The flask was removed from the glove box and bubbled with air for 35 min. The crude was concentrated by rotary evaporation, then diluted with $CH_2Cl_2$ and chromatographed over basic alumina using $CH_2Cl_2$ mobile phase. The eluent was collected and the solvent was removed by rotary evaporation. The resulting polymer was dissolved in a minimum amount of $CH_2Cl_2$, and precipitated into a large excess of 1-propanol. The polymer was allowed to settle, the liquid fraction was decanted, and the polymer was rinsed with a fresh portion of 1-propanol, then methanol. The polymer was again dissolved in $CH_2Cl_2$ and collected by precipitation into 5° C. methanol, filtered, and then rinsed with fresh methanol. The product was dried at ambient temperature under vacuum overnight resulting in 32.50 g (61%) of a white solid. GPC (THF, polystyrene standards) Mn 43,994, Mw/Mn 1.27.

Copolymer Synthesis

Polypropylene molds were vacuum de-gassed at 90° C. prior to use. The molds were placed in a nitrogen atmosphere glove box immediately after degassing. The monomers, cross-linker and initiator were combined as indicated in Table 1, then placed under low vacuum to remove any trapped air bubbles, back-flushed with nitrogen, and immediately placed in the glove box. The monomer formulation was dispensed into vacuum de-gassed polypropylene molds using a syringe equipped with a 1-μm glass-fiber filter. The filled molds were placed in a convection oven for 1 h at 70° C., then 2 hrs at 110° C. The resulting polymer samples were extracted in refluxing acetone for 6 hours, rinsed and air dried, then placed under vacuum at 65° C. for 15 hrs. Tensile properties and microvacuole resistance results are listed in Table 2.

TABLE 1

Formulation Component Detail

| ID | PEA (wt %) | PEMA (wt %) | BzMA (wt %) | BDDA (wt %) | oMTP (wt %) | EX. 1 (wt %) | EX. 2 (wt %) | EX. 3 (wt %) | EX. 4 (wt %) |
|---|---|---|---|---|---|---|---|---|---|
| 0 | 65.0 | 30.0 | — | 3.2 | 1.8 | — | — | — | — |
| 1 | 55.25 | 25.50 | — | 2.72 | 1.53 | 15.00 | — | — | — |
| 2 | 55.25 | 25.50 | — | 2.72 | 1.53 | — | — | 15.00 | — |
| 3 | 79.00 | — | — | 1.00 | — | 20.00 | — | — | — |
| 4 | 79.00 | — | — | 1.00 | — | — | — | 20.00 | — |
| 5 | 69.00 | — | — | 1.00 | — | 29.99 | — | — | — |
| 6 | 69.00 | — | — | 1.00 | — | — | — | 30.00 | — |
| 7 | 78.98 | — | — | 1.02 | — | — | 19.99 | — | — |
| 8 | 68.99 | — | — | 1.02 | — | — | 29.99 | — | — |
| 9 | 63.97 | — | 15.00 | 1.00 | — | — | 20.00 | — | — |
| 10 | 89.00 | — | — | 1.00 | — | — | — | — | 10.00 |
| 11 | 79.00 | — | — | 1.00 | — | — | — | — | 20.00 |

TABLE 2

Formulation Component Detail

| ID | PEA (wt %) | PEMA (wt %) | BzMA (wt %) | BDDA (wt %) | oMTP (wt %) | EX. 5 (wt %) | EX. 6 (wt %) | EX. 7 (wt %) |
|---|---|---|---|---|---|---|---|---|
| 12 | 78.99 | — | — | 1.01 | — | 20.00 | — | — |
| 13 | 88.97 | — | — | 1.03 | — | — | 10.00 | — |
| 14 | 78.98 | — | — | 1.00 | — | — | 20.02 | — |
| 15 | 78.98 | — | — | 1.03 | — | — | — | 19.99 |
| 16 | 68.99 | — | — | 1.01 | — | — | — | 30.00 |

TABLE 3

Tensile and Thermal Properties, % EWC, RI, and Glistening Test Results

| ID | Stress at Break (MPa) | Strain at Break (MPa) | Young's Modulus (MPa) | 25% Secant Modulus (MPa) | 100% Secant Modulus (MPa) | EWC (%) | Glistenings |
|---|---|---|---|---|---|---|---|
| 0 | 8.12 | 104 | 57.30 | — | 7.51 | 0.30 | Yes |
| 1 | 9.14 | 113 | 87.29 | 14.98 | 7.63 | 0.71 | No |
| 2 | 8.18 | 134 | 51.35 | 9.31 | 5.38 | 2.38 | No |
| 3 | 3.66 | 188 | 5.40 | 1.69 | 0.99 | 1.02 | No |
| 4 | 3.80 | 196 | 4.01 | 1.42 | 0.87 | 2.78 | No |
| 5 | 3.84 | 181 | 7.36 | 2.08 | 1.20 | 1.57 | No |
| 6 | 3.54 | 187 | 4.18 | 1.48 | 0.92 | 4.08 | No |
| 7 | 3.22 | 183 | 5.25 | 1.65 | 0.96 | 1.23 | No |
| 8 | 3.75 | 186 | 7.91 | 2.18 | 1.18 | 1.78 | No |
| 9 | 7.04 | 207 | 31.31 | 5.62 | 2.25 | 1.22 | very few |
| 10 | 3.62 | 200 | 3.49 | 1.35 | 0.81 | 2.27 | No |
| 11 | 3.76 | 197 | 3.91 | 1.45 | 0.87 | 3.84 | No |
| 12 | 2.38 | 175 | 3.23 | 1.22 | 0.77 | 2.57 | No |
| 13 | 3.91 | 194 | 4.19 | 1.53 | 0.95 | 0.82 | very few |
| 14 | 5.17 | 198 | 8.17 | 2.46 | 1.42 | 1.31 | very few |
| 15 | 5.93 | 186 | 14.27 | 4.29 | 2.40 | 0.77 | many |
| 16 | 8.25 | 169 | 37.94 | 10.44 | 4.78 | 1.02 | many |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A polymeric ophthalmic or otorhinolaryngological device material comprising a) 65 to 95% (w/w) of a monofunctional acrylate or methacrylate monomer of formula [1]:

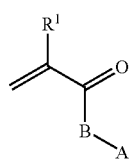

[1]

wherein
B=—O(CH$_2$)$_n$—, —(OCH$_2$CH$_2$)$_n$—; —NH(CH$_2$)$_n$—, or —NCH$_3$(CH$_2$)$_n$—;
R$^1$=H, CH$_3$, CH$_2$CH$_3$, or CH$_2$OH;
n=0-12;
A=C$_6$H$_5$ or O(CH$_2$)$_m$C$_6$H$_5$, where the C$_6$H$_5$ group is optionally substituted with —(CH$_2$)$_n$H, —O(CH$_2$)$_n$H, —CH(CH$_3$)$_2$, —C$_6$H$_5$, —OC$_6$H$_5$, —CH$_2$C$_6$H$_5$, F, Cl, Br, or I; and
m=0-18;

b) a difunctional acrylate or methacrylate cross-linking monomer of formula [2]:

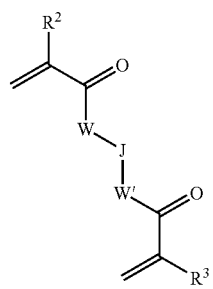

[2]

wherein
R$^2$, R$^3$ independently=H, CH$_3$, CH$_2$CH$_3$, or CH$_2$OH;
W, W' independently=O(CH$_2$)$_d$, NH(CH$_2$)$_d$, NCH$_3$(CH$_2$)$_d$, O(CH$_2$)$_d$C$_6$H$_4$, O(CH$_2$CH$_2$O)$_d$CH$_2$, O(CH$_2$CH$_2$CH$_2$O)$_d$CH$_2$, O(CH$_2$CH$_2$CH$_2$CH$_2$O)$_d$CH$_2$, or nothing;
J=(CH$_2$)$_a$, O(CH$_2$CH$_2$O)$_b$, O, or nothing, provided that if W and W'=nothing, then J≠nothing;
d=0-12;
a=1-12; and
b=1-24;
and c) 5 to 35% (w/w) of a di-block or tri-block macromer of formula [3a], [3b], [3c], [3d], or [3e]:

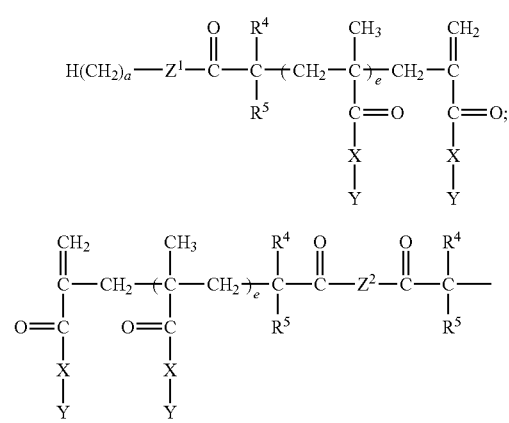

[3a]

[3b]

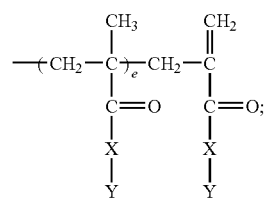

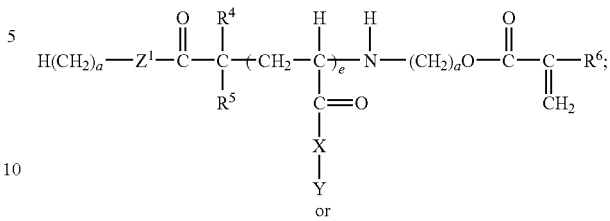

[3c]

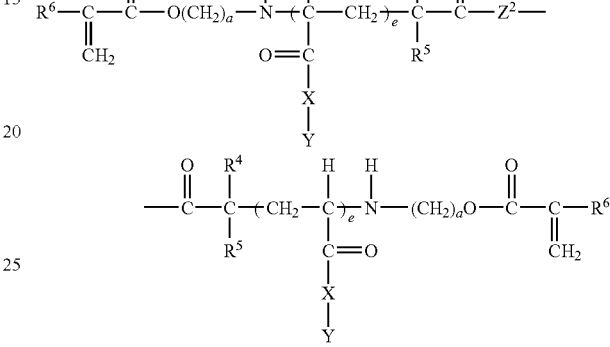

[3d]

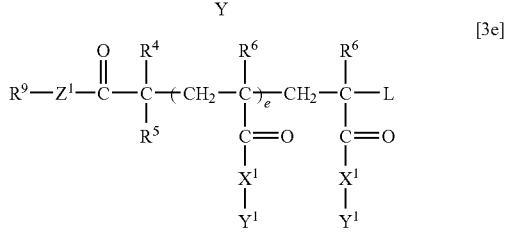

[3e]

wherein for formulas [3a], [3b], [3c], [3d], and [3e]
a independently=1-18;
Z$^1$=—(OCH$_2$CH$_2$)$_p$O—, —(OCH$_2$CH(CH$_3$))$_p$O—, —(NHCH$_2$CH$_2$)$_p$NH—, or —N(COR$^7$)CH$_2$CH$_2$)$_p$O;
X=O, NH—, N(CH$_3$)—, N(CH$_2$CH$_3$)—, or N(C$_6$H$_5$)—;
Y=—(CH$_2$)$_a$H, —CH$_2$C(CH$_3$)$_2$; —CH$_2$CH$_2$N(C$_6$H$_5$)$_2$, —CH$_2$CH(OH)CH$_2$OC$_6$H$_5$, —(CH$_2$CH$_2$O)$_p$C$_6$H$_5$, —(CH$_2$)$_t$C$_6$H$_5$, or —(CH$_2$)$_t$OC$_6$H$_5$;
Z$^2$=—(OCH$_2$CH$_2$)$_p$O—, —(OCH$_2$CH(CH$_3$))$_p$O—, —(NHCH$_2$CH$_2$)$_p$NH—, or —O(CH$_2$CH$_2$(COR$^7$)N)$_p$—R$^8$—(N(COR$^7$)CH$_2$CH$_2$)$_p$O—;
R$^4$, R$^5$, R$^6$ independently=H, CH$_3$, CH$_2$CH$_3$, CH$_2$CH$_2$CH$_3$, CH(CH$_3$)$_2$, CH$_2$CH$_2$CH$_2$CH$_3$, or CH$_2$CH(CH$_3$)$_2$;
R$^7$=CH$_3$, CH$_2$CH$_3$, CH$_2$CH$_2$CH$_3$, CH(CH$_3$)$_2$, CH$_2$CH$_2$CH$_3$, or CH$_2$CH(CH$_3$)$_2$;
R$^8$=CH$_2$, (CH$_2$)$_2$, (CH$_2$)$_3$, (CH$_2$)$_4$, (CH$_2$)$_5$, or (CH$_2$)$_6$;
p=1-500;
e=1-200, provided that p≧e;
t=0-6;
R$^9$=CH$_2$=C(R$^6$)C(O)—, CH$_2$=C(R$^6$)CO$_2$CH$_2$CH$_2$NHC(O)—, or CH$_2$=CHC$_6$H$_4$C(O)CH$_2$=CHC$_6$H$_4$CH$_2$; and
L=H, Cl, Br, —CH$_2$C(O)CH$_3$, CH$_2$C(O)C(CH$_3$)$_3$, —CH$_2$C(O)C$_6$H$_5$, —CH$_2$C(O)C$_6$H$_4$OH, —CH$_2$C(O)C$_6$H$_4$OCH$_3$,

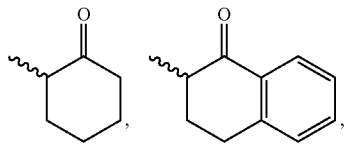

or CH₂CH=CH₂.

2. The polymeric device material of claim 1 wherein for the monomer of formula [1]:
B=—O(CH₂)ₙ— or —(OCH₂CH₂)ₙ—;
R¹=—H or —CH₃;
n=1-5;
A=—C₆H₅ or —O(CH₂)ₘC₆H₅; and
m=0-4.

3. The polymeric device material of claim 1 wherein for the monomer of formula [2]:
R², R³ independently=H or CH₃;
W, W' independently=O(CH₂)_d, O(CH₂)_dC₆H₄, or nothing;
J=O(CH₂CH₂O)_b or nothing, provided that if W and W'=nothing, then J≠nothing;
d=0-6; and
b=1-10.

4. The polymeric device material of claim 1 wherein for the macromer of formula [3a], [3b], [3c], [3d] or [3e]:
a independently=1-12;
Z¹=—(OCH₂CH₂)_pO—, or —(OCH₂CH(CH₃))_pO—;
X=O, or N(CH₃)—;
Y=—(CH₂)_tC₆H₅, or (CH₂)_tOC₆H₅;
Z²=—(OCH₂CH₂)_pO—, or —(OCH₂CH(CH₃))_pO—;
R⁴, R⁵, R⁶ independently=H, CH₃, or CH₂CH₃;
p=20-250;
e=5-150, provided that p≧e;
t=1-4;
R⁹=CH₂=C(R⁶)C(O)—, or CH₂=C(R⁶)CO₂CH₂CH₂NHC(O)—; and
L=H, Cl, Br, —CH₂C(O)CH₃, CH₂C(O)C(CH₃)₃, —CH₂C(O)C₆H₅, —CH₂C(O)C₆H₄OH, —CH₂C(O)C₆H₄OCH₃,

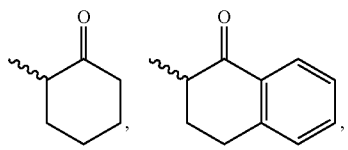

or CH₂CH=CH₂.

5. The polymeric device material of claim 4 wherein for the macromer of formula [3a], [3b], [3c], [3d], or [3e]:
a independently=1-4;
Z¹=—(OCH₂CH₂)_pO—;
X=O;
Y=(CH₂)_tC₆H₅;
Z²=—(OCH₂CH₂)_pO—;
R⁴, R⁵=CH₃;
R⁶=H or CH₃;
p=30-120;
e=10-100, provided that p is ≧e;
t=1-2;
R⁹=CH₂=C(R⁶)C(O)—, or CH₂=C(R⁶)CO₂CH₂CH₂NHC(O)—; and

L=H, —CH₂C(O)C₆H₅, —CH₂C(O)C₆H₄OH, —CH₂C(O)C₆H₄OCH₃, CH₂CH=CH₂.

6. The polymeric device material of claim 1 wherein the monomer of formula [1] is selected from the group consisting of benzyl methacrylate; 2-phenylethyl methacrylate; 3-phenylpropyl methacrylate; 4-phenylbutyl methacrylate; 5-phenylpentyl methacrylate; 2-phenoxyethyl methacrylate; 2-(2-phenoxyethoxy)ethyl methacrylate; 2-benzyloxyethyl methacrylate; 2-(2-(benzyloxy)ethoxy)ethyl methacrylate; 3-benzyloxypropyl methacrylate; benzyl acrylate; 2-phenylethyl acrylate; 3-phenylpropyl acrylate; 4-phenylbutyl acrylate; 5-phenylpentyl acrylate; 2-phenoxyethyl acrylate; 2-(2-phenoxyethoxy)ethyl acrylate; 2-benzyloxyethyl acrylate; 2-(2-(benzyloxy)ethoxy)ethyl acrylate; and 3-benzyloxypropyl acrylate.

7. The polymeric device material of claim 1 wherein the monomer of formula [2] is selected from the group consisting of ethylene glycol dimethacrylate; diethylene glycol dimethacrylate; triethylene glycol dimethacrylate; 1,6-hexanediol dimethacrylate; 1,4-butanediol dimethacrylate; 1,4-benzenedimethanol dimethacrylate; ethylene glycol diacrylate; diethylene glycol diacrylate; triethylene glycol diacrylate; 1,6-hexanediol diacrylate; 1,4-butanediol diacrylate; and 1,4-benzenedimethanol diacrylate.

8. The polymeric device material of claim 1 wherein the amount of monomer [1] is 70 to 90% (w/w).

9. The polymeric device material of claim 1 wherein the amount of monomer [2] is 0.5 to 3% (w/w).

10. The polymeric device material of claim 1 wherein the amount of the di-block or tri-block macromer is 10 to 30% (w/w).

11. The polymeric device material of claim 10 wherein the amount of the di-block or tri-block macromer is 10 to 20% (w/w).

12. The polymeric device material of claim 1 wherein the di-block or tri-block macromer is a macromer of formula [3a].

13. The polymeric device material of claim 1 wherein the di-block or tri-block macromer is a macromer of formula [3b].

14. The polymeric device material of claim 1 wherein the di-block or tri-block macromer is a macromer of formula [3c].

15. The polymeric device material of claim 1 wherein the di-block or tri-block macromer is a macromer of formula [3d].

16. The polymeric device material of claim 1 wherein the di-block or tri-block macromer is a macromer of formula [3e].

17. The polymeric device material of claim 1 further comprising an ingredient selected from the group consisting of a polymerizable UV absorbers and a polymerizable colorants.

18. The polymeric device material of claim 17 comprising 0.1-5% (w/w) of a polymerizable UV absorber and 0.01-0.5% (w/w) of a polymerizable colorant.

19. An ophthalmic or otorhinolaryngological device comprising the polymeric device material of claim 1 wherein the ophthalmic or otorhinolaryngological device is selected from the group consisting of intraocular lenses; contact lenses; keratoprostheses; corneal inlays or rings; otological ventilation tubes; and nasal implants.

20. The ophthalmic or otorhinolaryngological device of claim 19 wherein the ophthalmic or otorhinolaryngological device is an intraocular lens.

* * * * *